(12) United States Patent
Boucher et al.

(10) Patent No.: US 10,813,573 B2
(45) Date of Patent: Oct. 27, 2020

(54) BIOMECHANICAL ANALYSIS AND VALIDATION SYSTEM AND METHOD

(71) Applicant: LABORATOIRE VICTHOM INC., Laval (CA)

(72) Inventors: Sylvain Boucher, Laval (CA); Étienne Belzile, Québec (CA); Rudy Bélanger, St-Pacôme (CA); Gervais Constant, La Pocatière (CA); Louis Desrosiers, Québec (CA)

(73) Assignee: LABORATOIRE VICTHOM INC., Laval QC (CA)

( * ) Notice: Subject to any disclaimer, the term of this patent is extended or adjusted under 35 U.S.C. 154(b) by 362 days.

(21) Appl. No.: 15/738,577

(22) PCT Filed: Mar. 16, 2017

(86) PCT No.: PCT/CA2017/000055
§ 371 (c)(1),
(2) Date: Dec. 20, 2017

(87) PCT Pub. No.: WO2017/156617
PCT Pub. Date: Sep. 21, 2017

(65) Prior Publication Data
US 2018/0192922 A1    Jul. 12, 2018

Related U.S. Application Data

(60) Provisional application No. 62/308,604, filed on Mar. 15, 2016.

(51) Int. Cl.
*A61B 5/11* (2006.01)
*A61B 5/00* (2006.01)

(52) U.S. Cl.
CPC ............ *A61B 5/1121* (2013.01); *A61B 5/112* (2013.01); *A61B 5/1114* (2013.01); *A61B 5/1126* (2013.01); *A61B 5/1127* (2013.01); *A61B 5/6823* (2013.01); *A61B 5/6828* (2013.01); *A61B 5/6829* (2013.01); *A61B 5/1122* (2013.01); *A61B 2562/0219* (2013.01)

(58) Field of Classification Search
CPC ..... A61B 5/1121; A61B 5/1114; A61B 5/112; A61B 5/1126; A61B 5/1127; A61B 5/6823; A61B 5/6828; A61B 5/6829
USPC .......................................... 600/595
See application file for complete search history.

(56) References Cited

U.S. PATENT DOCUMENTS 4,228,745 A * 10/1980 Gale ........................ A47C 9/08
                                                        108/116
9,068,843 B1 * 6/2015 Sohn ......................... G06F 3/03
(Continued)

*Primary Examiner* — Daniel L Cerioni
(74) *Attorney, Agent, or Firm* — PRAXIS

(57) ABSTRACT

A biomechanical analysis and validation system and method suitable for clinical diagnosis while providing accurate measurements of the angles of lower body segments and joints (i.e. without undue drift error and gravity vector estimation error). The system and method use inertial sensors configured to be positioned at the pelvis, the right and left thigh, the right and left shank and the right and left foot, and, optionally plantar pressure sensors to be positioned under the right and left foot of a subject. Biomechanical information of the subject is provided by expressing the orientation of the inertial sensors with respect to the orientation of the lower body segments of the subject.

15 Claims, 18 Drawing Sheets

(56) References Cited

U.S. PATENT DOCUMENTS

| | | | |
|---|---|---|---|
| 2007/0055176 A1* | 3/2007 | Branch | A61B 5/4533 600/587 |
| 2010/0248921 A1* | 9/2010 | Shinomiya | A63B 23/0405 482/142 |
| 2010/0286575 A1* | 11/2010 | Ochi | A63B 22/16 601/5 |
| 2011/0275957 A1* | 11/2011 | Bhandari | A61B 34/20 600/595 |
| 2012/0046540 A1* | 2/2012 | Branch | A61B 5/4566 600/415 |

* cited by examiner

BIOMECHANICAL ANALYSIS AND VALIDATION SYSTEM AND METHOD

CROSS-REFERENCE TO RELATED APPLICATIONS

This application claims the benefits of U.S. provisional patent application No. 62/308,804 filed on Mar. 15, 2016, which is herein incorporated by reference.

TECHNICAL FIELD

The present disclosure relates to a biomechanical analysis and validation system and method.

BACKGROUND

Most of the systems that provide the most accurate measurements of the angles of body segments and joints are based on optical technologies. These systems are expensive and require a relatively large space for use and, although versatile, require complex management (i.e. calibration, data processing, etc.). Accordingly, they are more suitable for research than clinical diagnosis.

Inertial systems, used to capture motion for animation, are becoming more efficient and some manufacturers offer such systems for the measurement of the angles of body segments and joints for clinical diagnosis. However, these systems do not meet the necessary specifications (error of less than 1°), as opposed to foot or knee orthoses effects for correcting the knee joint problems.

These systems use attitude and heading reference systems (AHRS), which use different types of inertial sensors (gyroscope and accelerometer), with or without magnetic compass, data fusion algorithms.

These systems are designed to compensate for the angle drift error, which is caused by the integration of the gyroscopes' angular velocity, using the gravitational acceleration as a reference. In dynamic mode, such as during walking, the estimation of the orientation of the gravity vector is not possible since the gravitational acceleration is confused with the acceleration due to the motion of body segments. Several algorithms have been developed to minimize the loss of reference in dynamic mode but their effectiveness is limited in time. Although accelerometers help reduce the error due to the drift of the gyroscopes, these are still subject to error in dynamic mode and can always be seen as a source of error. In all cases, these systems juggle between the drift error and the estimation error of the gravity vector and produce an insufficient overall error.

Accordingly, there is a need for a system that provides accurate measurements of the angles of body segments and joints (i.e. without undue drift error and gravity vector estimation error) and is suitable for clinical diagnosis. Furthermore, there is a need for a biomechanical analysis and brace efficiency validation system and method using such body segments and joints measurements.

SUMMARY

A general object of the present disclosure is to provide a biomechanical analysis and validation system and method that is suitable for clinical diagnosis while providing accurate measurements of the angles of body segments and joints (i.e. without undue drift error and gravity vector estimation error).

Some of the advantages of the present disclosure are as follows:
  simplified diagnostic and validation;
  use by non-specialists;
  portability and accuracy
  provide personalized mechanical orthosis corrections from biomechanical data;
  validate the effectiveness of an orthosis before the patient leaves the clinic;
  allow patient and health care professional to visualize the immediate biomechanical effect of an orthosis, thus contributing to treatment compliance;
  avoid over-corrections that can cause premature wear in other joints;
  obtain a symmetrical walking pattern;
  adopt a biofeedback approach;
  provide a human performance optimization tool;
  ensure optimal reimbursement by insurance companies;
  provide a strategic tool for telemedicine.

The present disclosure provides a method for providing biomechanical information of a subject, comprising the steps of:
  positioning inertial sensors at the pelvis, the right and the left thighs, the right and the left shanks and the right and the left feet of the subject;
  aligning the lower body segments of the subject in a global reference system ($X_g$, $Y_g$, $Z_g$), where $X_g$ is defined by the anteroposterior axis, $Y_g$ is defined by the gravity vector and $Z_g$ is perpendicular to $X_g$ and $Y_g$;
  determining a quaternion $q_s^g$ expressing an orientation the lower body segments of the subject with respect to the global reference system;
  determining the orientation of the $Y_g^b$ axis of the inertial sensors with respect to the global reference system;
  determining the orientation of the $X_g^b$ axis of the inertial sensors with respect to the global reference system;
  determining the orientation of the $Z_g^b$ axis by calculating the vector product $Z_g^b = X_g^b \times Y_g^b$;
  determining a quaternion $q_g^b$ expressing a change of reference from the global reference system to a reference of the inertial sensors from $Y_g^b$, $X_g^b$ and $Z_g^b$;
  determining a quaternion $q_b^s$ expressing a change of reference of the inertial sensors with regard to the lower body segments of the subject by calculating $q_b^s = (q_b^g q_s^g)^*$;
  initializing gyroscopes of the inertial sensors using the reference of the inertial sensors with regard to the lower body segments of the subject;
  calculating angles of the lower body segments of the subject during a transition phase from a sitting posture to a standing posture of the subject using the data from the inertial sensors, providing an orientation of the lower body segments of the subject in the standing posture $q_{s_0}^g$ to be used as an initial value when recording locomotion cycle sessions of the subject; providing the angles of the lower body segments of the subject.

The present disclosure further provides a method of aligning the lower body segments of a subject in a global reference system, comprising the steps of:
  providing a body alignment system consisting of an adjustable height stool, a movable base, a right and a left foot positioning blocks and a right and a left knee spacers having a height adjustment mechanism;
  having the subject sit on the adjustable height stool;
  adjusting the eight of the adjustable height stool so that the subject's thighs are horizontal and the subject's shanks are vertical, with respect to the movable base, with the subjects feet aligned using the foot positioning blocks and the subjects knees are resting against the knee spacers;

positioning anatomical reference markers on the lower body segments of the subject at:
- the greater trochanter (GT);
- the lateral epicondyle (LE);
- the head of the fibula (HF);
- the lateral malleolus (LM);
- the anterior superior lilac spine (ASIS);
- the center of the patella (CP);

positioning as a reference marker at the center of the foot positioning blocks (CFPB);

projecting a horizontal and a vertical laser leveling beams on a side of the subject so as to pass by the LE and HF anatomical reference markers, respectively;

adjusting the position of the thighs of the subject by adjusting a height of the adjustable height stool such that the GT anatomical reference marker is level with the horizontal laser leveling beam;

adjusting the position of the shanks of the subject by adjusting a position of the foot positioning blocks such that the LM anatomical reference marker is level with the vertical laser leveling beam;

projecting a front of the subject vertical laser leveling beam so as to pass by the ASIS anatomical reference marker, the VLB vertical laser leveling beam being positioned such as to project a plan that is coplanar with the anteroposterior axis;

adjusting the position of the knees of the subject by adjusting the knee spacers such that the CP anatomical reference marker is level with the vertical laser leveling beam;

adjusting the position of the feet of the subject by adjusting the foot positioning blocks such that the CFPB reference marker is level with the vertical laser leveling beam VLB;

defining the quaternion $q_s^g$ of the orientation of the body segments of the subject with respect to the global reference system.

The present disclosure also provides a body alignment device, comprising:
- a movable base having positioned thereon:
  - an adjustable height stool;
  - a right and a left foot positioning blocks; and
  - a right and a left knee spacers having a height adjustment mechanism.

The present disclosure further provides a body alignment device as described above wherein the right and the left foot positioning blocks are provided with lateral, foot length and anteroposterior axis positioning adjustment mechanisms.

BRIEF DESCRIPTION OF THE FIGURES

Embodiments of the disclosure will be described by way of examples only with reference to the accompanying drawings, in which.

Similar references used in different Figures denote similar components.

DETAILED DESCRIPTION

Generally stated, the non-limitative illustrative embodiment of the present disclosure provides a biomechanical analysis and validation system and method that is suitable for clinical diagnosis while providing accurate measurements of the angles of body segments and joints (i.e. without undue drift error and gravity vector estimation error). The system and method enable health professionals (MDs, clinicians, surgeons, physiotherapists, orthotists, etc.) to design orthotic solutions taking into account the biomechanical characteristics of a subject and validate those solutions to ensure optimum efficiency. Furthermore, the system and method enable health professionals to evaluate the effects of corrective surgeries or exercise programs.

Clinical assessments by health professionals today are still very empirical. Traditionally, the assessment of subjects' biomechanical dysfunction as well as of orthoses, surgery or exercise programs is more qualitative than quantitative. Anthropometric measurements and biomechanical evaluations are usually carried out using hand measurement tools, without quantitative method to objectify the results.

Figure 1:
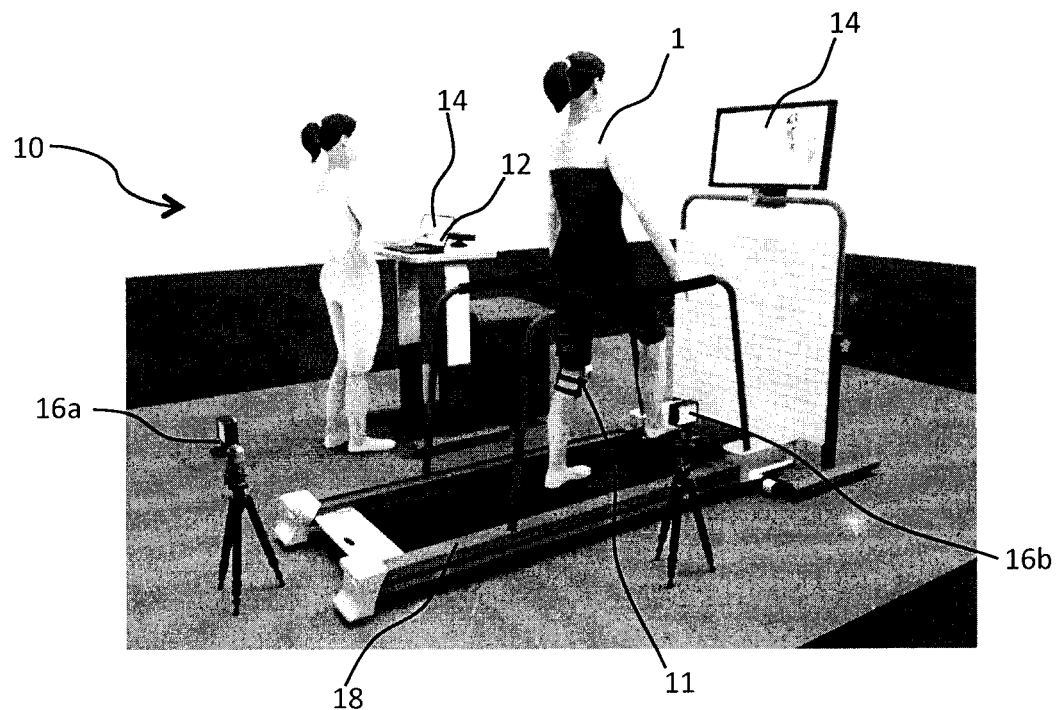
FIG. 1 is a biomechanical analysis and validation system in accordance with an illustrative embodiment of the present disclosure.

The biomechanical analysis and validation system and method is an instrument that can be used to facilitate the identification of lower limbs biomechanical dysfunctions and validate orthotic solutions provided to patients as well as evaluate the effects of corrective surgeries or exercise programs. Referring to FIG. 1, the biomechanical analysis and validation system 10 includes a computing device 12 having one or more associated user interface/display 14, cameras positioned in the anteroposterior 16a and transversal 16b axes, a treadmill 18, or other such mechanism or walking path allowing a subject 1 to walk thereon, and sensors configured to be positioned on the subject 1.

Figure 2:
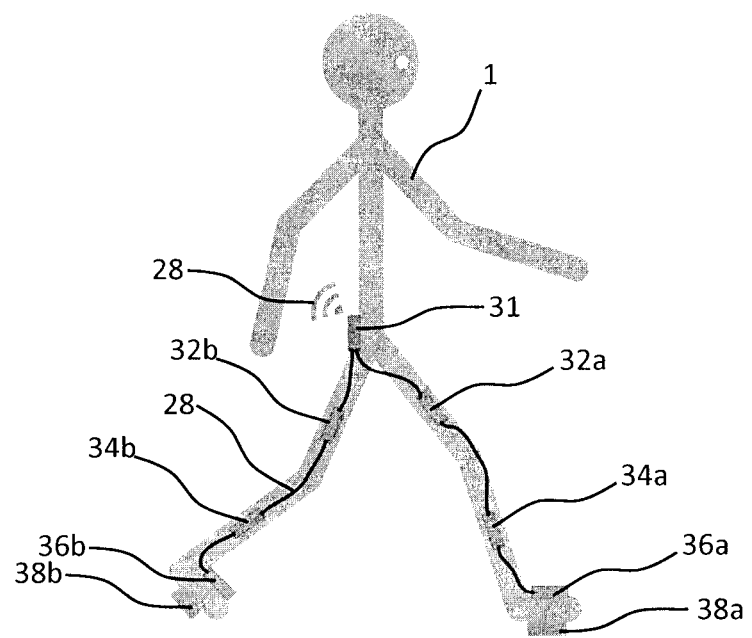
FIG. 2 is a schematic representation of the placement of the biomechanical sensors on a subject.

Referring to FIG. 2, the sensors consist in inertial sensors configured to be positioned at the pelvis 31, the right 32a and left 32b thigh, the right 34a and left 34b shank and the right 36a and left 38b foot, and planter pressure sensors to be positioned under the right 38a and left 38b foot. The precise positioning of the inertial sensors 31, 32a, 32b, 34a, 34b, 36a, 36b on their respective anatomical structure may vary from one subject to another. Advantageously, the position is selected so to minimize artifacts due to the motion of tissue relative to the skeleton. As for the plantar pressure sensors 38a, 38b, these may be multi-zone pressure sensors or be composed of a plurality of pressure sensors.

The size and position of plantar pressure sensors 38a, 38b are key for the mapping efficiency on both feet. An example of plantar pressure sensor size and positioning that can be used is disclosed in U.S. Pat. No. 7,137,998 entitled "Positioning of Lower Extremities Artificial Proprioceptors" by Victhom Human Bionics Inc, which uses four specifically placed plantar pressure sensors (two under each foot) in order to provide stable and rich signals.

In the illustrative embodiment, the inertial sensors 31, 32a, 32b, 34a, 34b, 36a, 36b are provided with the following:
  three-axis gyroscope;
  three-axis accelerometer;
  magnetic three-axis compass
  attitude and heading reference system (AHRS);
  precalibration
  bias compensation;
  synchronization input; and
  clock with an accuracy of at least 20 ppm.
An example of an inertial sensor that can be used is the VN-100 from VectorNav.

Figure 3:
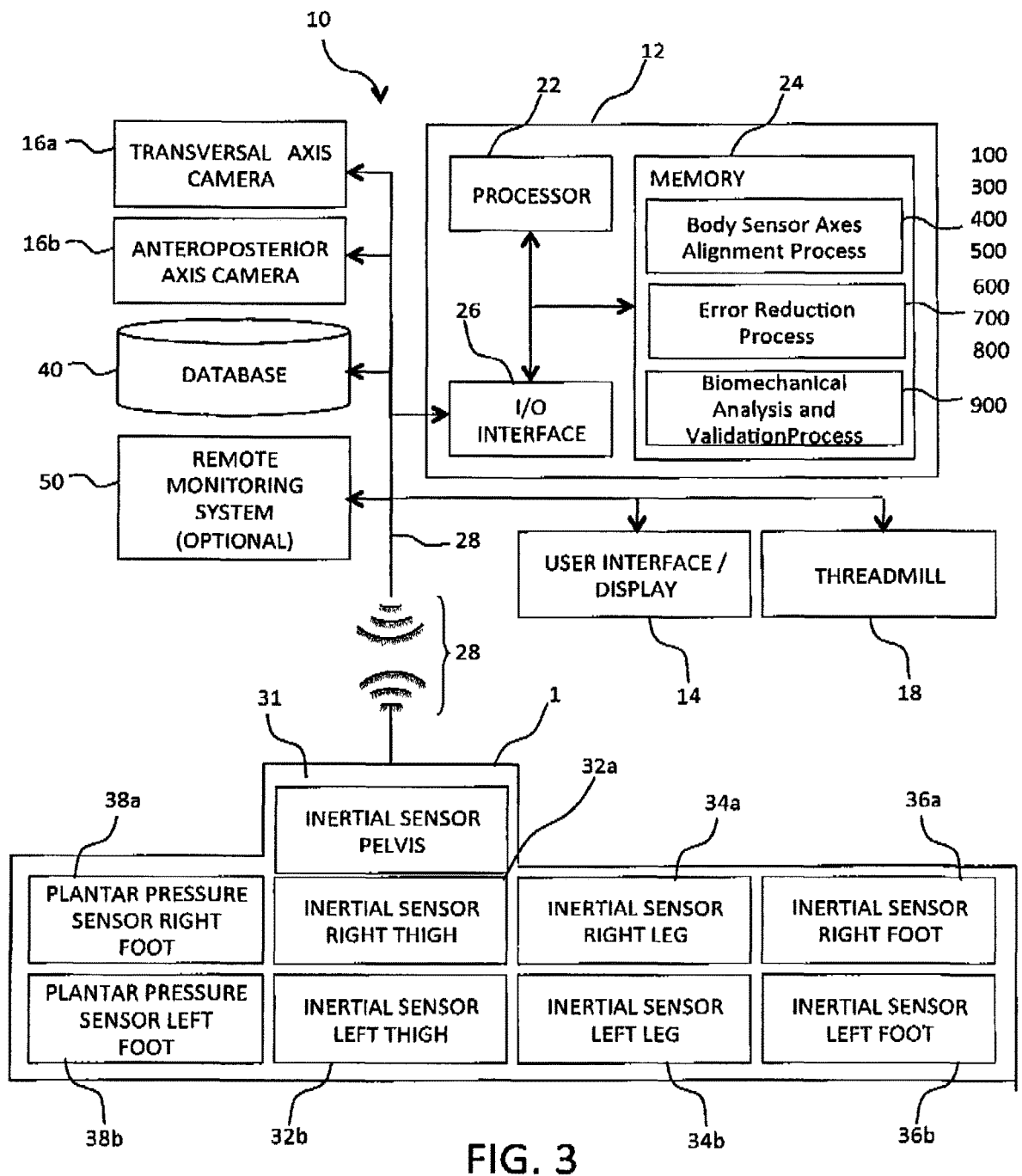
FIG. 3 is a schematic diagram of the biomechanical analysis and validation system of FIG. 1.

Referring now to FIG. 3, the computing device 12 includes a processor 22 with an associated memory 24 having stored therein processor executable instructions for configuring the processor 22 to perform various processes, namely the body sensor axes alignment process 100, 300, 400, 500, the error reduction process 600, 700, 800 and the biomechanical analysis and validation process 900, which processes will be further described below. The biomechanical analysis and validation system 10 further includes an input/output (I/O) interface 26 for communication with inertial sensors 31, 32a, 32b, 34a, 34b, 36a, 36b, plantar pressure sensors 38a, 38b, cameras 16a, 16b, database 40 and remote consulting system 50 (such as for telemedicine applications) through communication link 28, which may be wired, wireless or a combination of both.

Body Sensor Axes Alignment

Figure 4A:
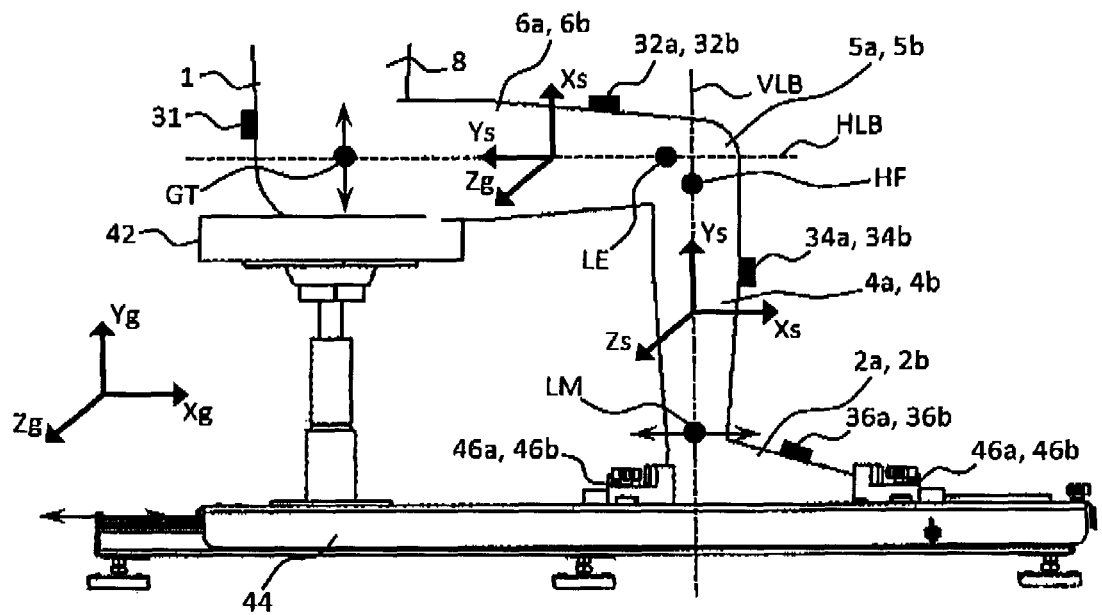
FIGS. 4A, 4B and 4C are a schematic representation of the lower body segments alignment procedure.
Figure 4B:
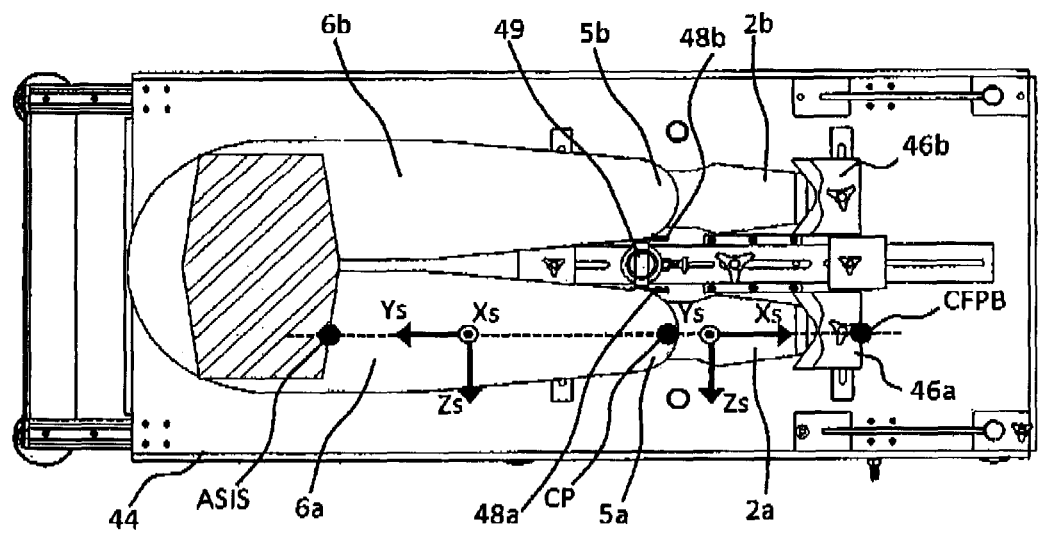
Figure 4C:
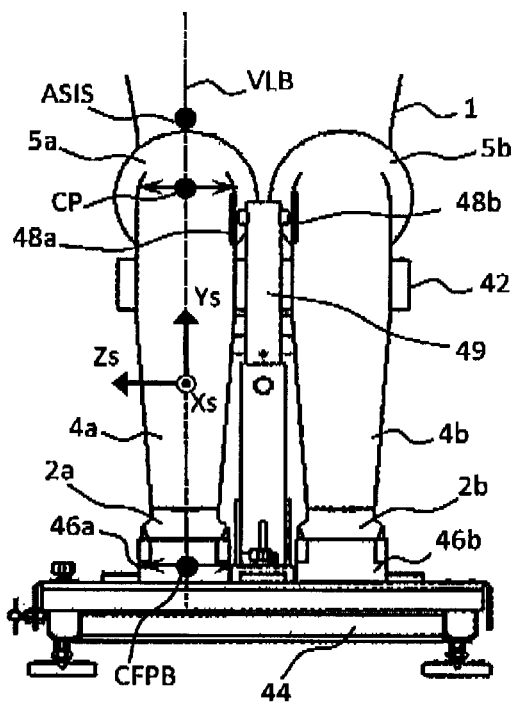

The virtual alignment of the inertial sensors 31, 32a, 32b, 34a, 34b, 36a, 36b on the body axes of the subject 1 (anteroposterior, transverse and longitudinal) takes place by aligning the lower body segments of the subject with regard to a global reference system. Referring to FIGS. 4A to 4C, the virtual alignment takes place using a body alignment system 40 consisting of an adjustable height stool 42, a movable base 44, right 46a and left 48b foot positioning blocks and right 48a and left 48b knee spacers having a height adjustment mechanism 49.

Figure 4D:
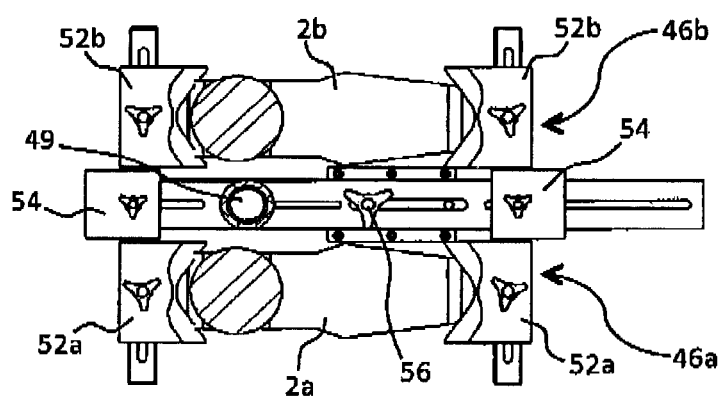
FIG. 4D is a schematic representation of the foot positioning blocks.

With reference to FIG. 4D, the foot positioning blocks 46a, 46b are provided with lateral 52a, 52b, foot length 54 and anteroposterior axis positioning 54 adjustment mechanisms in order to properly position the feet 2a, 2b of the subject 1 on the movable base 44.

Once the inertial sensors 31, 32a, 32b, 34a, 34b, 36a, 38b have been placed on the subject 1, the subject 1 is positioned on the body alignment system 40, sitting on the adjustable height stool 42 adjusted so that his thighs 8a, 6b are horizontal and his shanks 4a, 4b are vertical, with respect to the movable base 44 (i.e. ground), with feet 2a, 2b aligned using the foot positioning blocks 46a, 46b and knees 5a, 5b resting against the knee spacers 48a, 48b.

Figure 5:
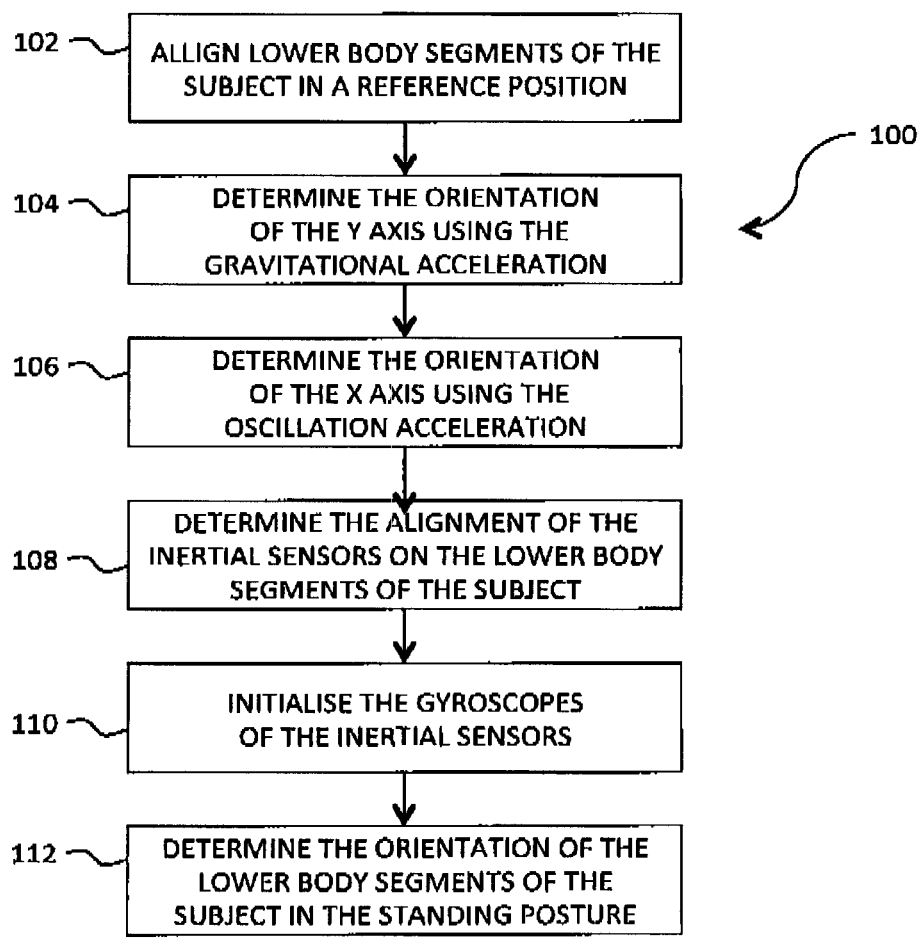
FIG. 5 is a flow diagram of the body sensor axes alignment process in accordance with an illustrative embodiment of the present disclosure.
Figure 6:
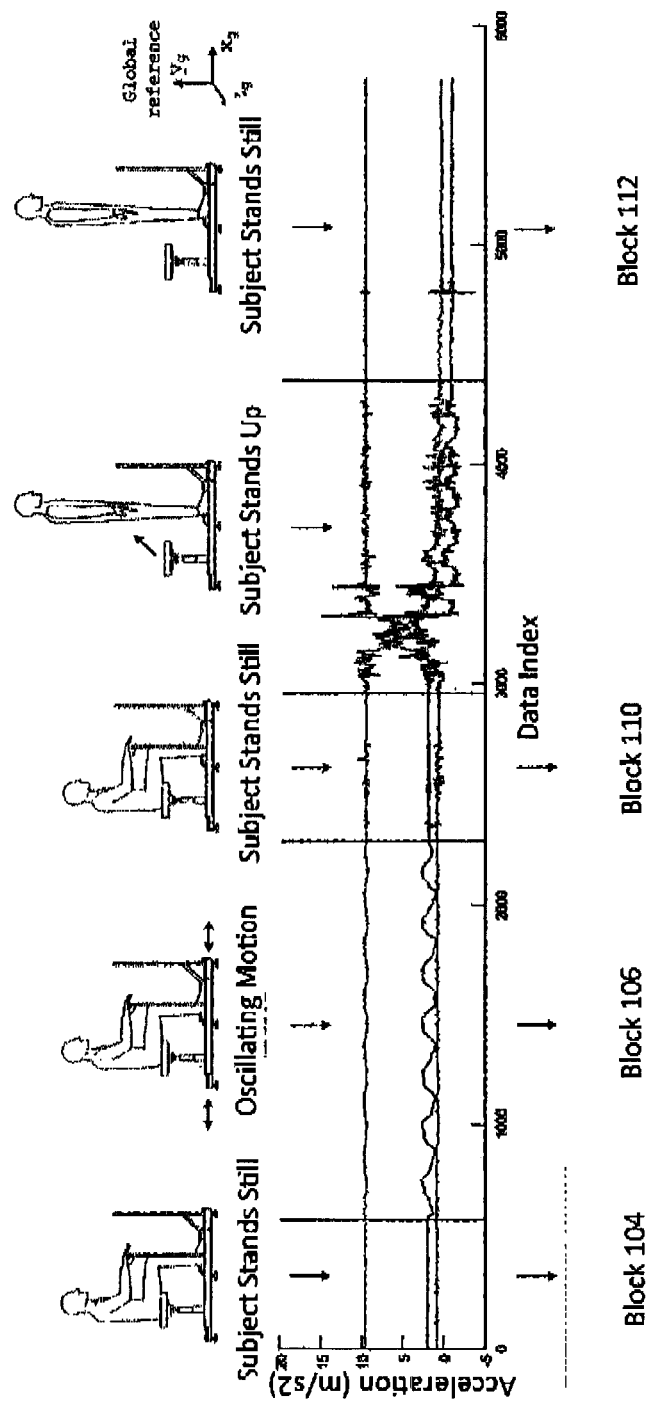
FIG. 6 is a schematic representation of the steps performed by the body sensor axes alignment process.
Figure 7:
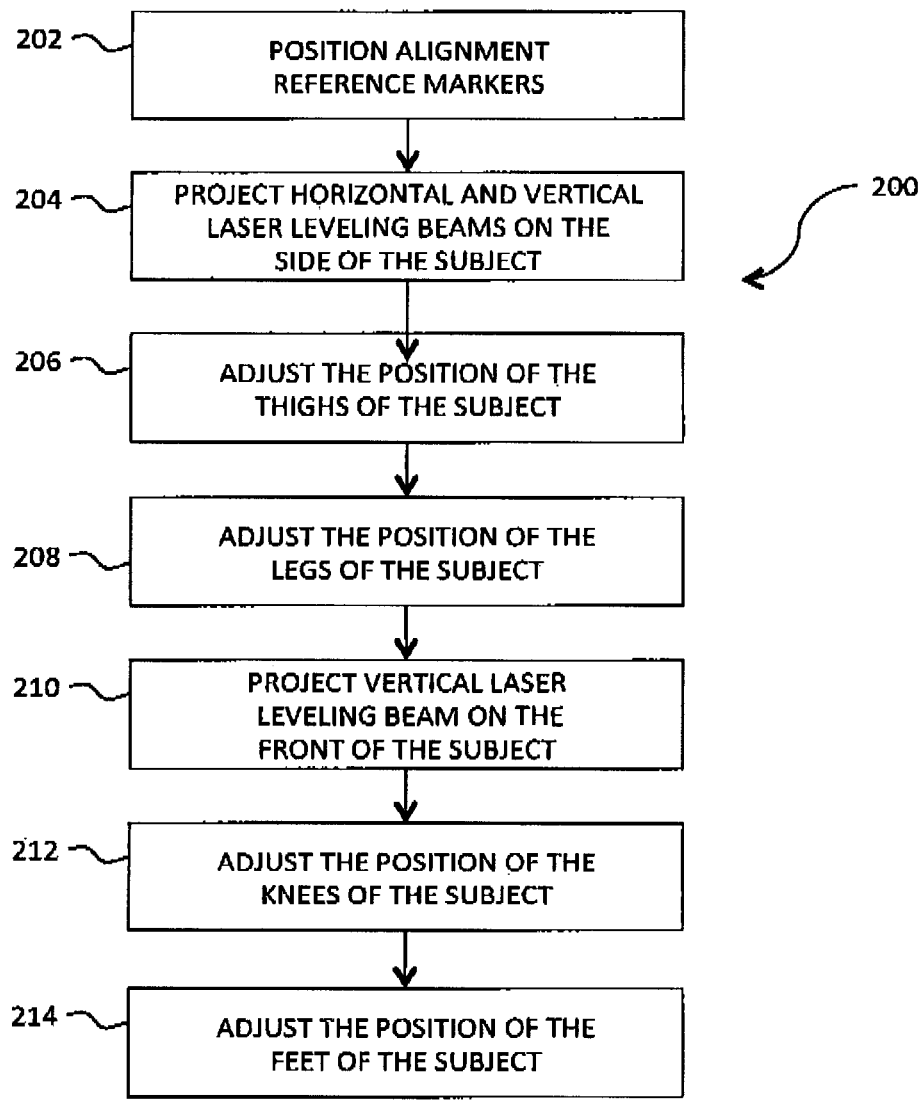
FIG. 7 is a flow diagram of the preliminary lower body segment alignment sub-process.

Referring to FIG. 5, with further reference to FIG. 7, there is shown a flow diagram of the body sensor axes alignment process 100 in accordance with an illustrative embodiment of the present disclosure, executed by the processor 22 (see FIG. 3). Steps of the process 100 are indicated by blocks 102 to 112.

The process 100 starts at block 102 where the lower body segments of the subject are aligned in a global reference system $(X_g, Y_g, Z_g)$, where $X_g$ is defined by the anteroposterior axis, $Y_g$ is defined by the gravity vector and $Z_g$ is perpendicular to $X_g$ and $Y_g$. The orientation of the body segments of the subject 1 $(X_s, Y_s, Z_s)$ with respect to the global reference system $(X_g, Y_g, Z_g)$ is provided by the quaternion $q_s^g$, which is obtained by executing the preliminary body segment alignment sub-process, which will be detailed further below.

At block 104, the orientation of the $Y_g^b$ axis of the inertial sensors 31, 32a, 32b, 34a, 34b, 38a, 38b reference with respect to the global reference system in the is determined by having the subject 1 remain motionless on the adjustable height stool 42, for a short duration, for example 5 seconds. The one-second period with the smallest variance in the accelerometer data from the inertial sensors 31, 32a, 32b, 34a, 34b, 36a, 38b is then identified in order to calculate the mean acceleration $\bar{A}$ for all lower body segments of the subject 1. The vector $\bar{A}$ corresponds to the gravity vector, which is also the vector of the $Y_g^b$.

At block 106, the orientation of the $X_g^b$ axis is determined by moving the subject 1, while remaining motionless on the adjustable height stool 42, in the anteroposterior axis (i.e. the $X_g$ axis of the global reference system $(X_g, Y_g, Z_g)$) by means of the movable base 44. Between about 7 and 10 oscillations are performed. The $X_g^b$ axis is determined by finding the axis that best fits the point cloud of the accelerometer data from the inertial sensors 31, 32a, 32b, 34a, 34b, 36a, 36b.

Then, at block 108, the alignment of the inertial sensors 31, 32a, 32b, 34a, 34b, 36a, 36b on the lower body segments is determined. First, the orientation of the $Z_g^b$ axis is determined by calculating the vector product of $Y_g^b$ and $X_g^b$, i.e. $Z_g^b = X_g^b \times Y_g^b$. Then, from this orthonormal basis, it is possible to calculate the quaternion $q_g^b$ of the change of reference from the global reference system ($X_g$, $Y_g$, $Z_g$) to the reference of the inertial sensors 31, 32a, 32b, 34a, 34b, 36a, 36b ($X_b$, $Y_b$, $Z_b$).

Since the orientation quaternion $q_s^g$ of the lower body segments of the subject 1 ($X_s$, $Y_s$, $Z_s$) with respect to the global reference system ($X_g$, $Y_g$, $Z_g$) is known by the position imposition of the adjustable height stool 42, it is possible to calculate the change in the reference of the inertial sensors 31, 32a, 32b, 34a, 34b, 36a, 30b with regard to the lower body segments, that is the alignment of the inertial sensors 31, 32a, 32b, 34a, 34b, 36a, 36b on the lower body segments:

$$q_b^s = (q_g^b q_s^g)^*$$

At block 110, the gyroscopes of the inertial sensors 31, 32a, 32b, 34a, 34b, 38a, 36b are initialized using the known orientation of the lower body segments of the subject 1. Since the orientation of the lower body segments during the sitting posture is known, it can be used to initialize the angles of the integrator of the gyroscopes of the inertial sensors 31, 32a, 32b, 34a, 34b, 36a, 36b.

Finally, at block 112, the integrator then calculates the angles of the lower body segments during the transition phase while the subject 1 goes from the sitting posture to the standing posture using the inertial sensors 31, 32a, 32b, 34a, 34b, 36a, 38b. The angles of the lower body segments of the subject 1 in the standing posture can then be estimated by taking a one-second data group having the least variance. The orientation of the lower body segments of the subject 1 in the standing posture $q_{s_0}^g$ is then saved to be used as the initial value when recording locomotion cycle sessions.

Referring to FIG. 7, with further reference to FIGS. 4A to 4C, there is shown a flow diagram of the preliminary lower body segments alignment sub-process 200 in accordance with an illustrative embodiment of the present disclosure. Steps of the sub-process 200 are indicated by blocks 202 to 214.

The sub-process 200 starts at block 202 where anatomical reference markers are positioned on the lower body segments of the subject 1, namely at:

the greater trochanter GT;
the lateral epicondyle LE;
the head of the fibula HF;
the lateral malleolus LM;
the anterior superior iliac spine ASIS; and
the center of the patella CP,
as well a further reference marker positioned at the center of the foot positioning blocks CFPB.

It is to be understood that other similarly aligned anatomical reference markers may be used with the disclosed preliminary lower body segments alignment procedure to obtain similar results.

At block 204, once the markers are positioned, a horizontal HLB and vertical VLB laser leveling beams are projected on the side of the subject 1 so as to pass by the LE and HF anatomical reference markers, respectively (see FIG. 4A).

Then, at block 206, the position of the thighs 6a, 6b of the subject 1 is adjusted by adjusting the height of the adjustable height stool 42 such that the GT anatomical reference marker is level with the horizontal laser leveling beam HLB.

At block 208, the position of the shanks 4a, 4b of the subject 1 is adjusted by adjusting the position of the foot positioning blocks 46a, 46b such that the LM anatomical reference marker is level with the vertical laser leveling beam VLB.

At block 210, the vertical laser leveling beam VLB is projected on the front of the subject 1 so as to pass by the ASIS anatomical reference marker (see FIG. 4C). It should be noted that the VLB is positioned such as to project a plan that is coplanar with the anteroposterior axis (i.e. the $X_g$).

Then, at block 212, the position of the knees 5a, 5b of the subject 1 is adjusted by adjusting the knee spacers 48a, 48b such that the CP anatomical reference marker is level with the vertical laser leveling beam VLB.

And finally, at block 214, the position of the feet 2a, 2b of the subject 1 is adjusted by adjusting the foot positioning blocks 46a, 46b such that the CFPB reference marker is level with the vertical laser leveling beam VLB.

It is to be understood that blocks 212 and 214 are performed for each knee 5a, 5b and foot 2a, 2b of the subject 1.

It is then possible to define by the quaternion $q_s^g$ the orientation of the body segments of the subject 1 with respect to the global reference system ($X_g$, $Y_g$, $Z_g$).

Figure 8:
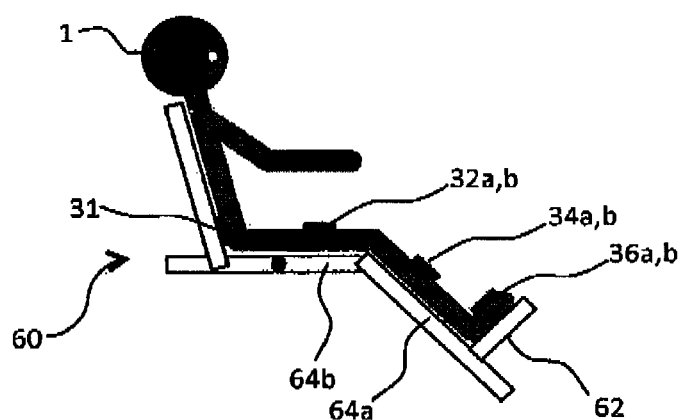
FIG. 8 is a schematic representation of the placement of a subject on the tilting/sliding mechanism.
Figure 9A:
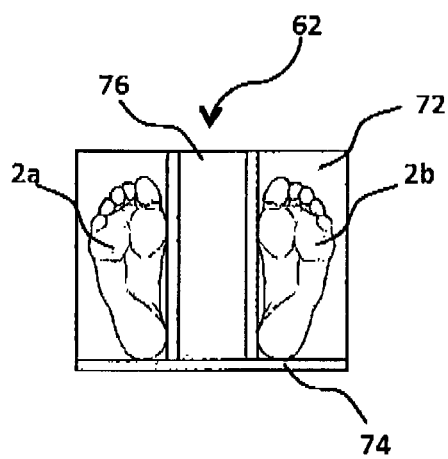
FIGS. 9A and 9B are a bottom and side views, respectively, of the footrest with a subject positioned thereon.
Figure 9B:
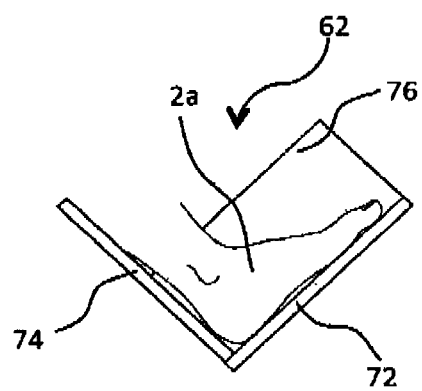

Referring to FIG. 8, there is shown an alternative embodiment of the virtual alignment of the inertial sensors 31, 32a, 32b, 34a, 34b, 36a, 36b on the body axes of the subject 1 (anteroposterior, transverse and longitudinal), which takes place using a tilting/sliding mechanism 60, for example a customized rocking chair. The subject 1 is positioned on the tilting/sliding mechanism 60 while ensuring that his shanks are resting upon the angled lower body support elements 64a, 64b and his feet are aligned in the anteroposterior axis using a footrest 62. Referring further to FIGS. 9A and 9B, the feet 2a, 2b of the subject 1 are supported and positioned by resting against bottom 72 and back 74 support elements as well as a central divider element 76. Thereafter, the subject 1 is displaced in the transverse axis (i.e. tilted or rocked) or anteroposterior six (i.e. slided) and either acceleration or angular velocity is measured.

The longitudinal, transverse and anteroposterior axis are determined by acquiring accelerometer and/or gyroscope data from the inertial sensors 31, 32a, 32b, 34a, 34b, 36a, 36b at different position or during motion and computing cross products of the resulting acceleration vectors and/or the mean axis of the angular velocities.

Figure 10:
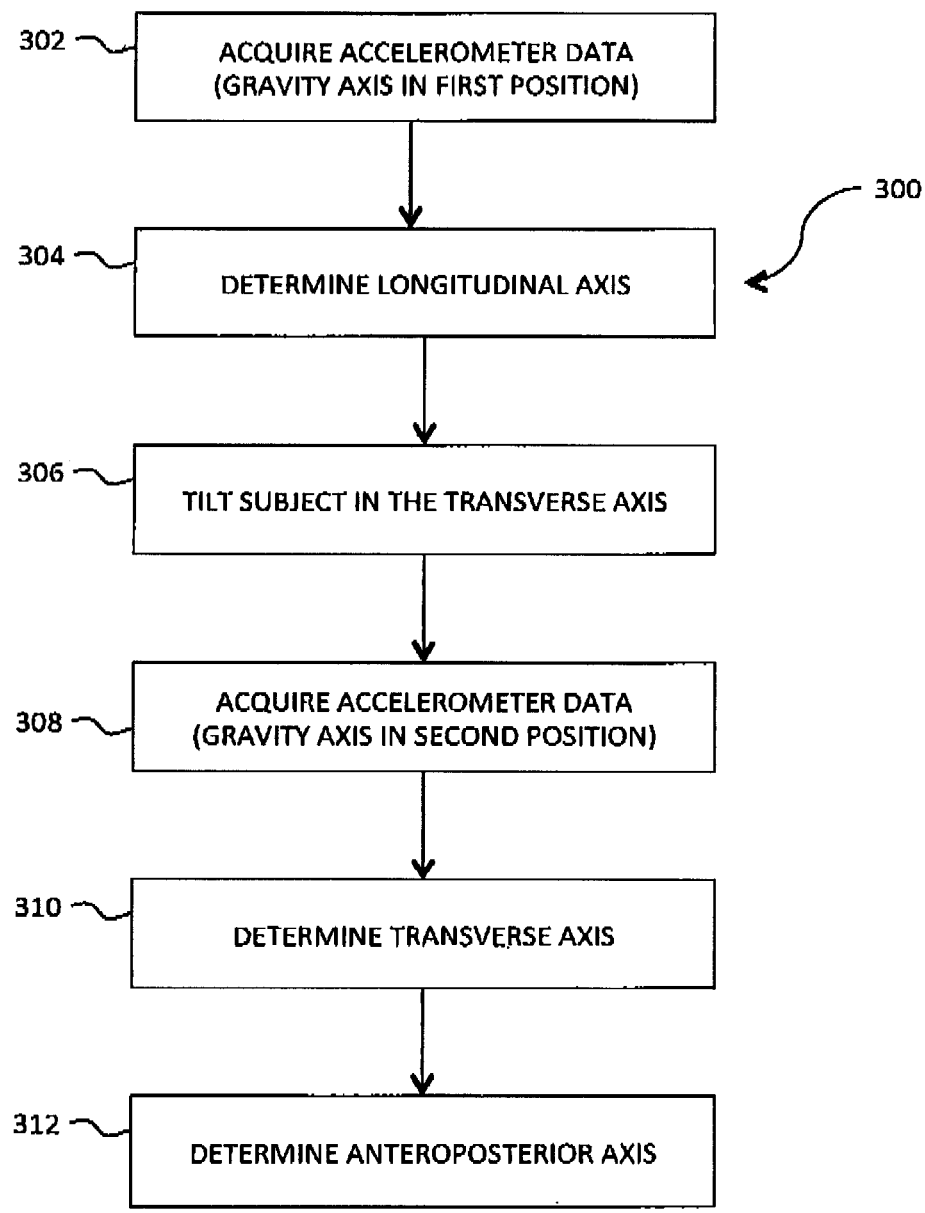
FIG. 10 is a flow diagram of the body sensor axes alignment process in accordance with a first illustrative embodiment of the present disclosure.
Figure 11:
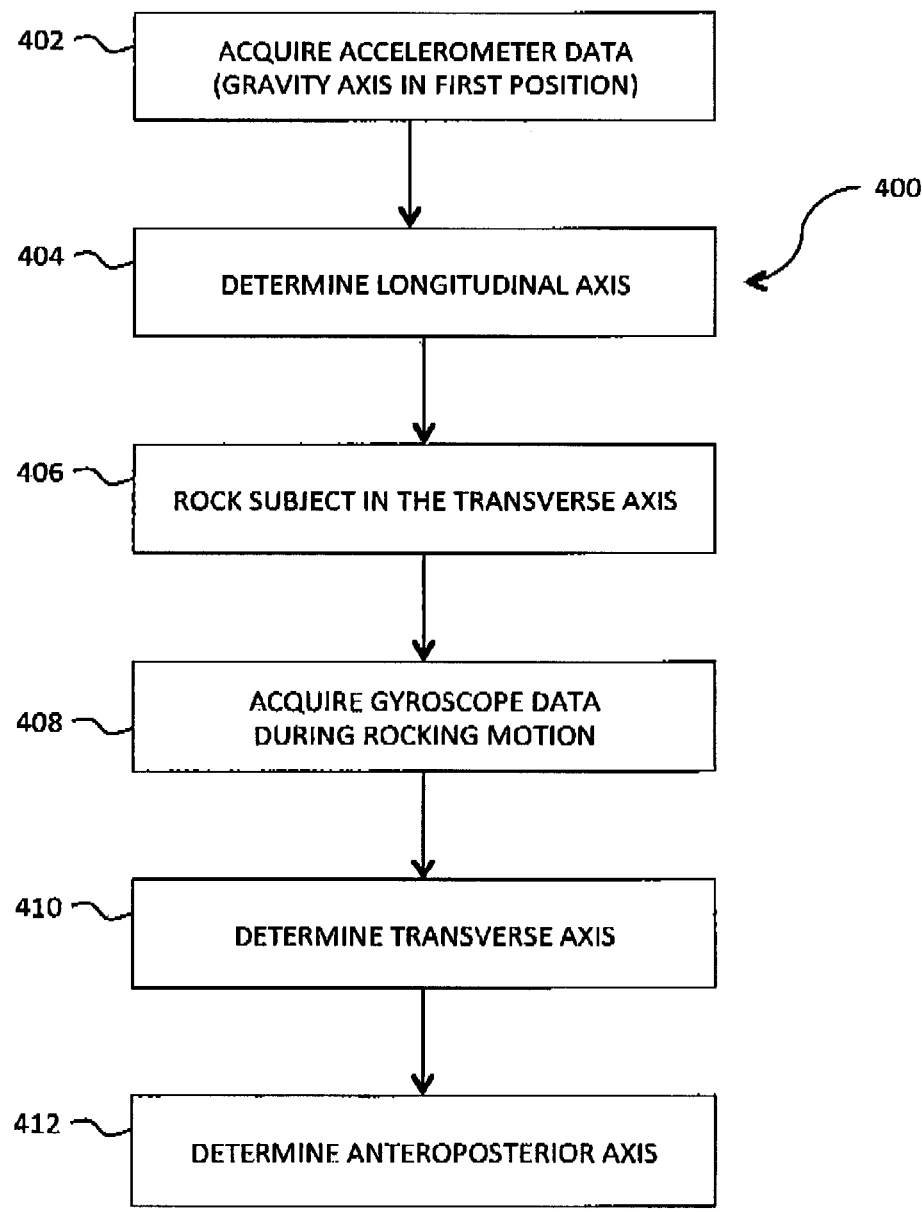
FIG. 11 is a flow diagram of the body sensor axes alignment process in accordance with a second illustrative embodiment of the present disclosure.
Figure 12:
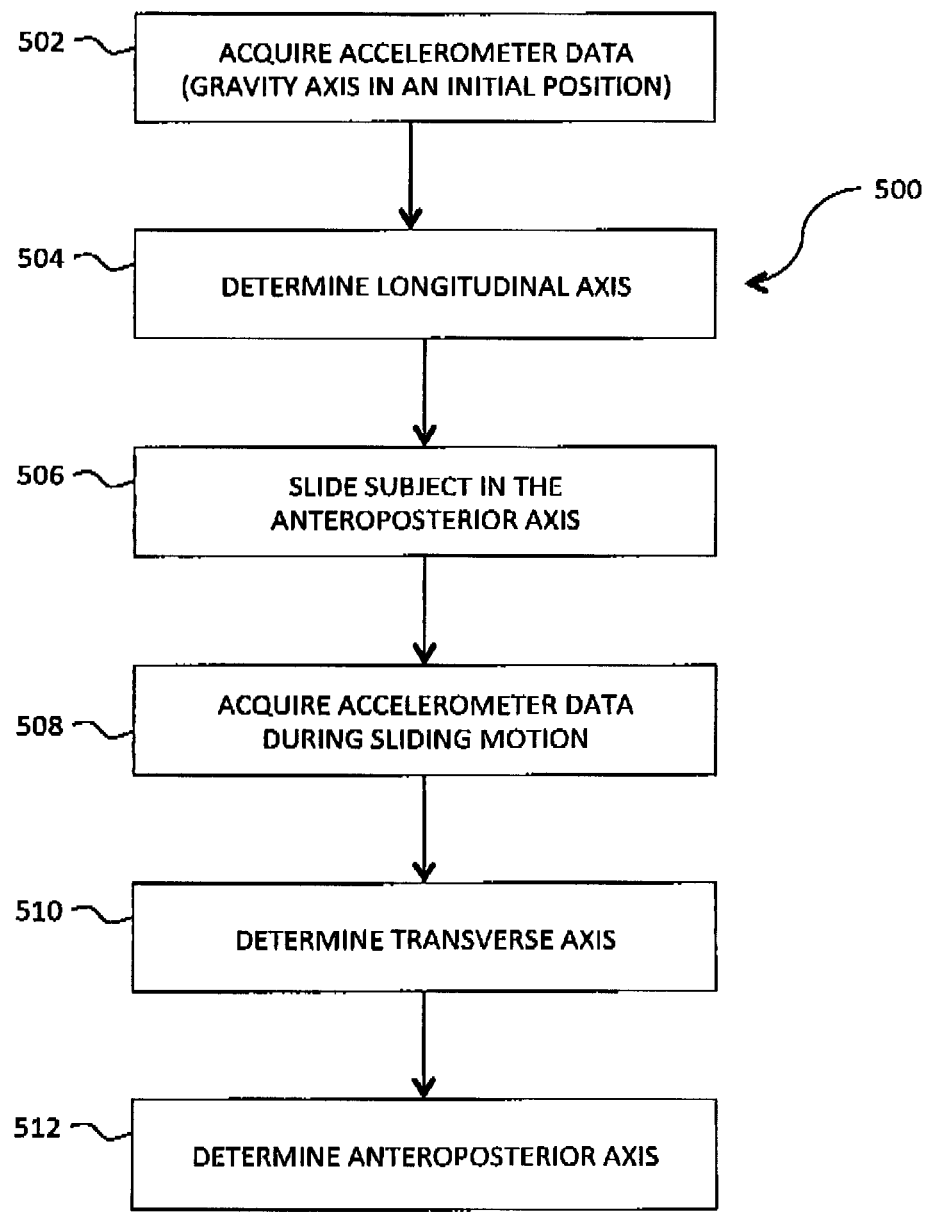
FIG. 12 is a flow diagram of the body sensor axes alignment process in accordance with a third illustrative embodiment of the present disclosure.

FIGS. 10 to 12 illustrate the body sensor axes alignment processes 300, 400, 500 in accordance with three alternative embodiments of the present disclosure, which are executed once the inertial sensors 31, 32a, 32b, 34a, 34b, 38a, 38b have been placed on the subject 1 and the subject 1 positioned on the tilting/sliding mechanism 60 with his shanks straight and his feet aligned using the footrest 62.

Figure 13:
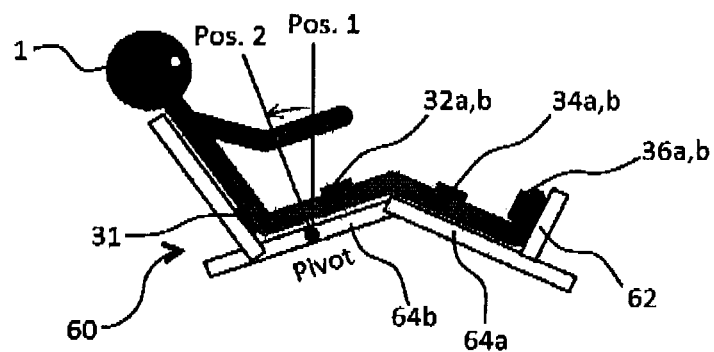
FIG. 13 is a schematic representation of the displacement of a subject on the tilting/sliding mechanism during the body sensor axes alignment process in accordance with the first illustrative embodiment of the present disclosure.

Referring to FIG. 10, with further reference to FIG. 13, there is shown a flow diagram of the first alternative embodiment of the body sensor axes alignment process 300 executed by the processor 22 (see FIG. 3). Steps of the process 300 are indicated by blocks 302 to 312.

The process 300 starts at block 302, where accelerometer data is acquired from the inertial sensors 31, 32a, 32b, 34a, 34b, 36a, 36b with the subject in a first position (Pos. 1 in FIG. 13), thus providing the gravity axis for the first position.

At block 304, the longitudinal axis is determined with the known angle of the lower limb segments of the subject 1 (i.e. angle when the subject 1 is in the first position with his lower limb segments resting upon the lower body support elements 64a, 64b).

Then, at block 306, the subject 1 is tilted in the transverse axis using the tilting/sliding mechanism 60 until it reaches a second position (Pos. 2 in FIG. 13).

At block 308, the accelerometer data is once more acquired, now with the subject 1 in the second position, thus providing the gravity axis for the second position.

At block 310, the transverse axis is determined by calculating the cross product of the gravity axis in the first and second positions.

Finally, at block 312, the anteroposterior axis is determined by calculating the cross product of the longitudinal and transverse axes.

Figure 14:
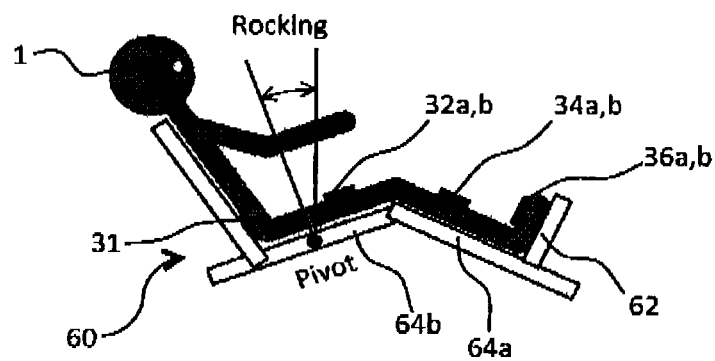
FIG. 14 is a schematic representation of the displacement of a subject on the tilting/sliding mechanism during the body sensor axes alignment process in accordance with the second illustrative embodiment of the present disclosure.
Figure 15:
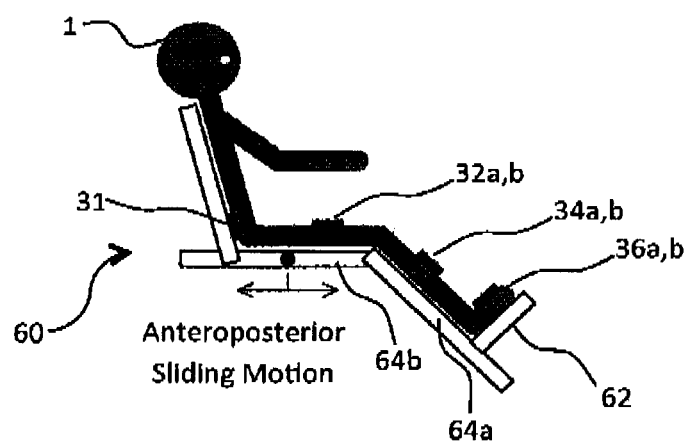
FIG. 15 is a schematic representation of the displacement of a subject on the tilting/sliding mechanism during the body sensor axes alignment process in accordance with the third illustrative embodiment of the present disclosure.

Referring now to FIG. 11, with further reference to FIG. 14, there is shown a flow diagram of the second alternative embodiment of the body sensor axes alignment process 400 executed by the processor 22 (see FIG. 3). Steps of the process 400 are indicated by blocks 402 to 412.

The process 400 starts at block 402, where accelerometer data is acquired from the inertial sensors 31, 32a, 32b, 34a, 34b, 36a, 36b with the subject 1 in an initial position, thus providing the gravity axis for the initial position.

At block 404, the longitudinal axis is determined with the known angle of the lower limb segments of the subject 1 (i.e. angle when the subject 1 is in the first position with his lower limb segments resting upon the lower body support elements 64a, 64b).

Then, at block 406, the subject 1 is rocked in the transverse axis using the tilting/sliding mechanism 60.

At block 408, gyroscope data is acquired from the inertial sensors 31, 32a, 32b, 34a, 34b, 36a, 36b during the rocking motion of the subject 1, thus providing the mean rotation axis.

At block 410, the transverse axis is determined from the mean rotation axis.

Finally, at block 412, the anteroposterior axis is determined by calculating the cross product of the longitudinal and transverse axes.

Figure 16:
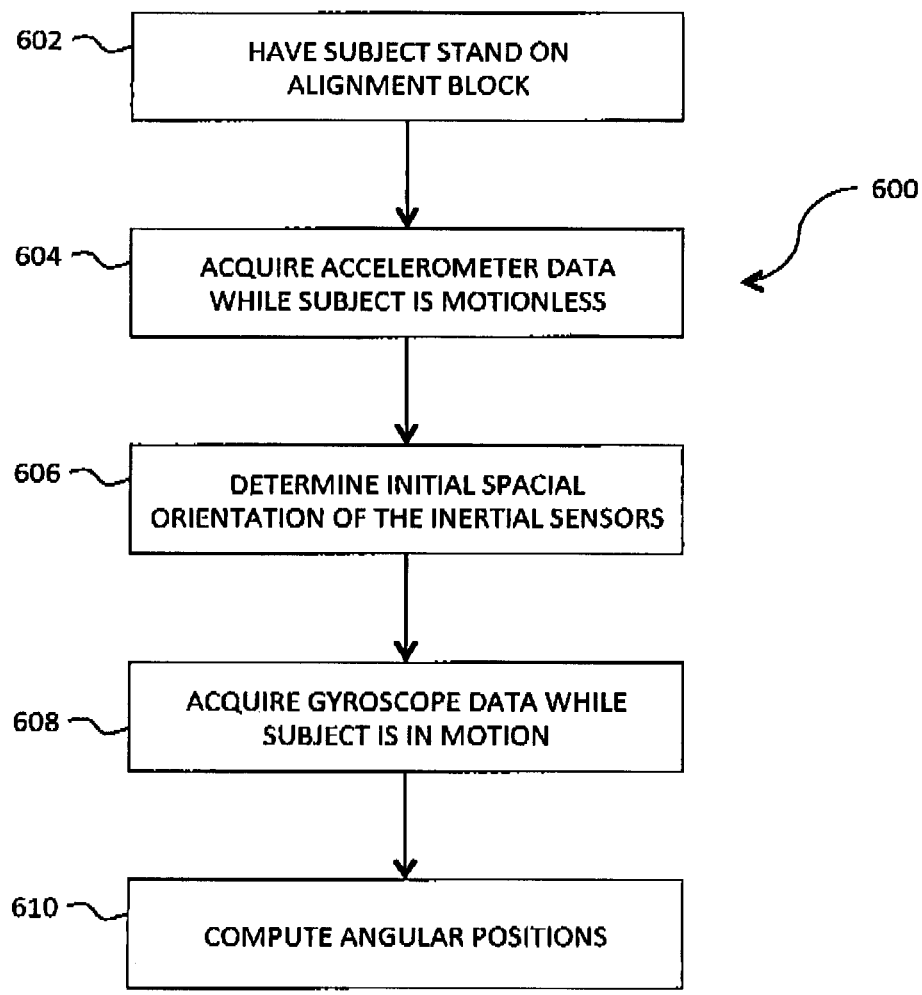
FIG. 16 is a flow diagram of the error reduction process in accordance with a first illustrative embodiment of the present disclosure.

Referring to FIG. 12, with further reference to FIG. 16, there is shown a flow diagram of the third alternative embodiment of the body sensor axes alignment process 600 executed by the processor 22 (see FIG. 3). Steps of the process 600 are indicated by blocks 502 to 512.

The process 500 starts at block 502, where accelerometer data is acquired from the inertial sensors 31, 32a, 32b, 34a, 34b, 36a, 36b with the subject 1 in an initial position, thus providing the gravity axis for the initial position.

At block 504, the longitudinal axis is determined with the known angle of the lower limb segments of the subject 1 (i.e. angle when the subject 1 is in the first position with his lower limb segments resting upon the lower body support elements 64a, 64b).

Then, at block 506, the subject 1 is slid in the anteroposterior axis using the tilting/sliding mechanism 60.

At block 508, the accelerometer data is once more acquired, now while the subject 1 during the sliding motion of the subject 1, thus providing the mean direction axis.

At block 510, the anteroposterior axis is determined from the mean direction axis.

Finally, at block 512, the transverse axis is determined by calculating the cross product of the longitudinal and anteroposterior axes.

It is to be understood that in further embodiments the operation of the tilting/eliding mechanism 60 can be performed manually and/or automatically by the biomechanical analysis and validation system 10.

Error Reduction

Since the objective of the biomechanical analysis and validation system 10 is to measure the angles of the joints of the lower limb segments with a minimum of about ten to fifteen steps, it is possible to limit the data acquisition to a period of about twenty to thirty seconds. Under these conditions, the use of gravity as a reference can be eliminated by ensuring that the gyroscopes of the inertial sensors 31, 32a, 32b, 34a, 34b, 36a, 36b are not derived during this time period. There are inertial systems that include gyroscopes calibration and drift compensation (Bias Compensation), which allow limiting angle drift to ±1° over a thirty second period.

Figure 17:
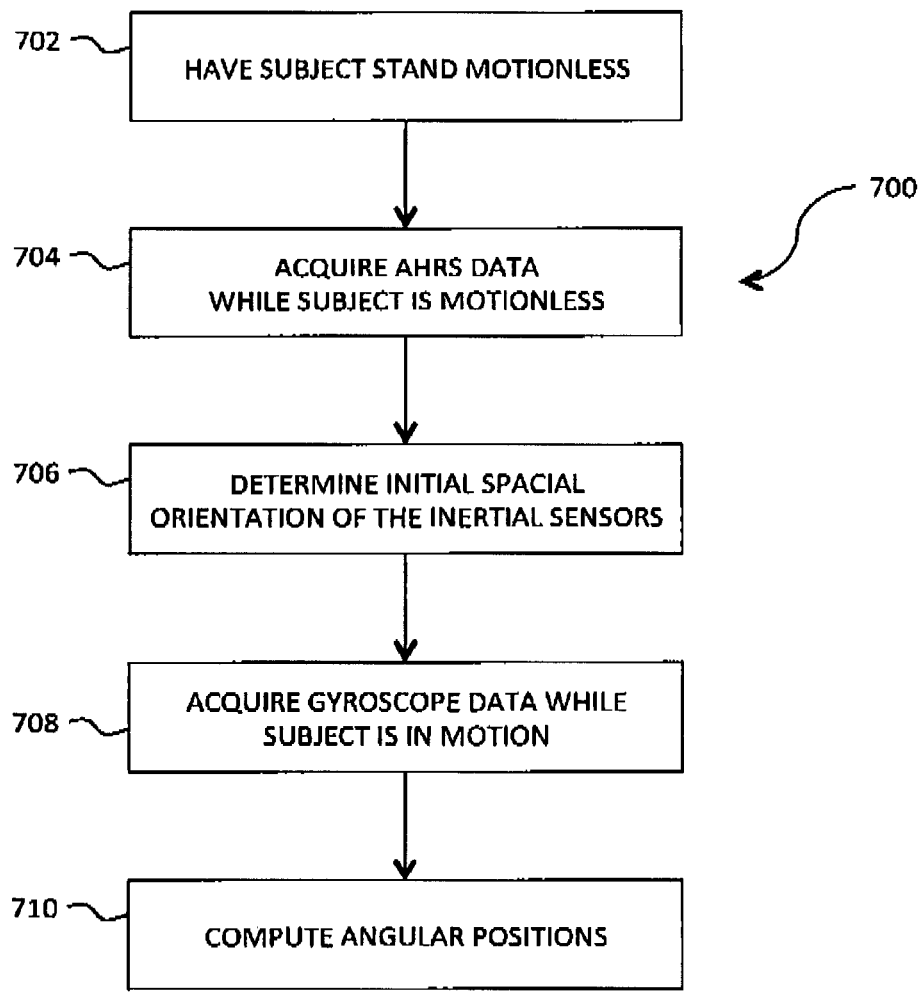
FIG. 17 is a flow diagram of the error reduction process in accordance with a second illustrative embodiment of the present disclosure.
Figure 18:
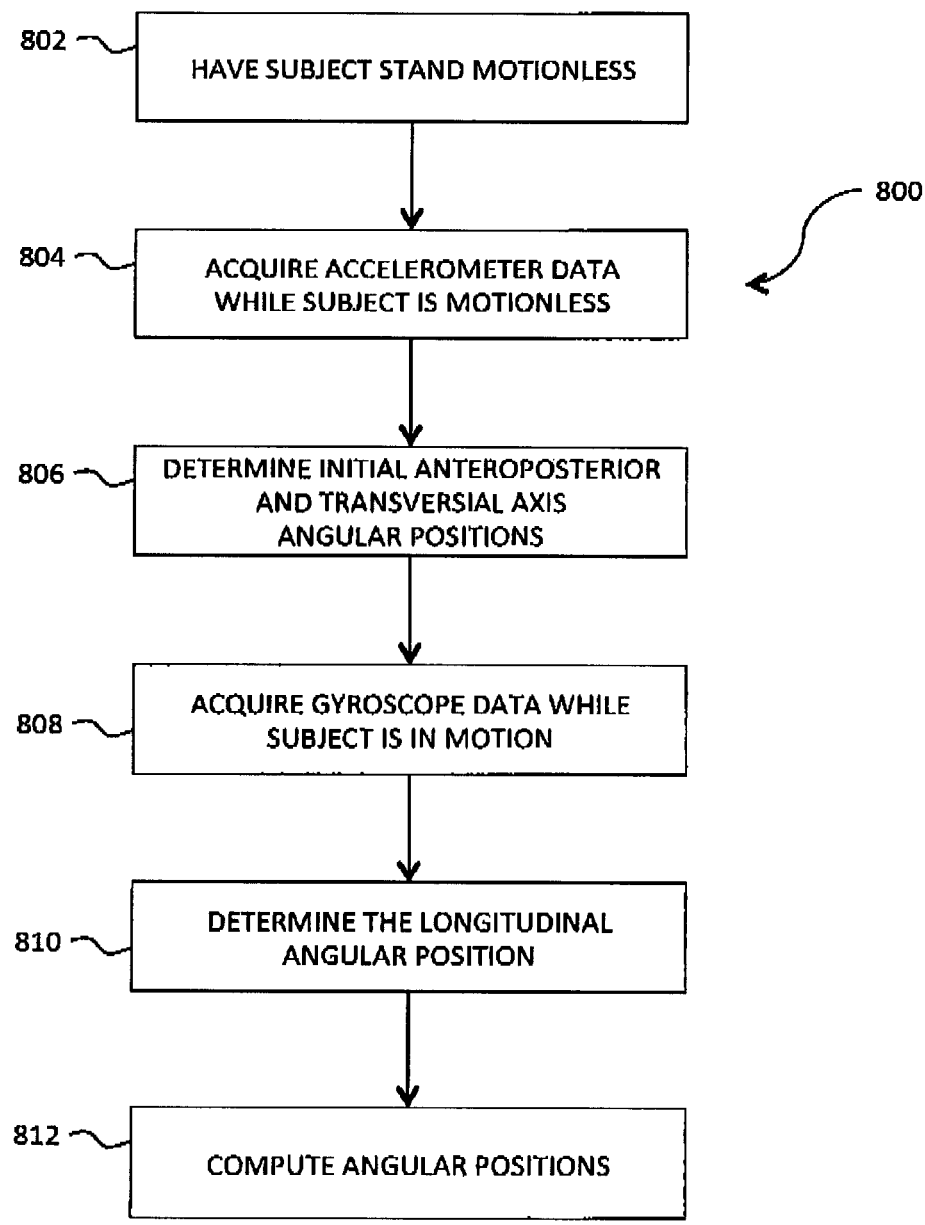
FIG. 18 is a flow diagram of the error reduction process in accordance with a third illustrative embodiment of the present disclosure.

FIGS. 16 to 18 illustrate three embodiments of the error reduction process 600, 700, 800, which are executed once the inertial sensors 31, 32a, 32b, 34a, 34b, 36a, 36b have been placed on the subject 1 and one of the body sensor axes alignment process 100, 300, 400, 500 has been executed.

Figure 19A:
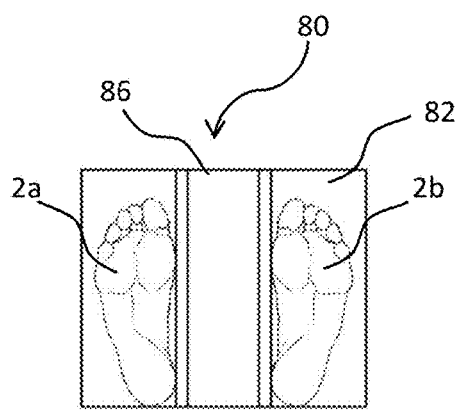
FIGS. 19A and 19B are a bottom and side views, respectively, of the alignment bloc with a subject positioned thereon.
Figure 19B:
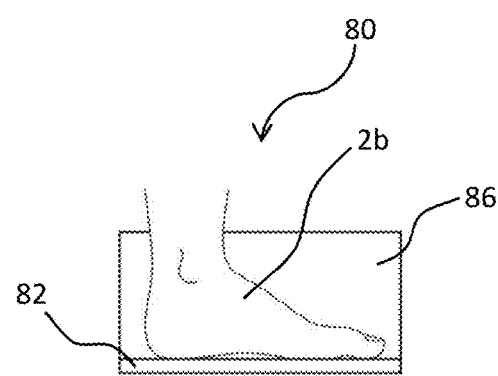

Referring to FIG. 18, with further reference to FIGS. 4D, 19A and 19B, there is shown a flow diagram of the first embodiment of the error reduction process 600 executed by the processor 22 (see FIG. 3). Steps of the process 600 are indicated by blocks 602 to 610.

The process 600 starts at block 602 where the feet 2a, 2b of the subject 1 are placed in the foot positioning blocks 46a, 46b, (see FIG. 4D), which have been removed from the body alignment system 40 (keeping their adjustments from the alignment procedure), while standing upright (in the case where body sensor axes alignment process 100 is used) or alignment block 80 (see FIGS. 19A and 19B) while the subject 1 is standing upright, his feet resting on 2a, 2b bottom support element 82 and spaced apart by central divider element 86 (in the case where body sensor axes alignment process 300, 400 or 500 is used).

At block 604, accelerometer data is acquired from the inertial sensors 31, 32a, 32b, 34a, 34b, 36a, 38b while the subject 1 is motionless and looking straight ahead.

Then, at block 606, the initial spatial orientation of the subject 1 is determined using the gravity vector obtained from the inertial sensors 31, 32a, 32b, 34a, 34b, 38a, 38b.

At block 608, gyroscopes data is acquired from the inertial sensors 31, 32a, 32b, 34a, 34b, 38a, 36b while the subject 1 is in motion, for example walking on the treadmill 18 of the biomechanical analysis and validation system 10 (see FIG. 1).

Finally, at block 610, the angular positions of lower limb segments of the subject 1 are computed by integrating the angular velocities over a 30 seconds period using the initial spatial orientation determined at block 606.

The error reduction process 600 is a simplification of current systems by solely using gyroscopes data during the dynamic phase (i.e. walking). This requires gyroscopes whose performances are high enough so as to allow the measurement of angular positions with an error of less than one degree per 30-second period.

Referring now to FIG. 17, there is shown a flow diagram of the second embodiment of the error reduction process 700 executed by the processor 22 (see FIG. 3). Steps of the process 700 are indicated by blocks 702 to 710.

The process 700 starts at block 702 where the subject 1 stands upright and motionless.

At block 704, attitude and heading reference systems (AHRS) data is acquired from the inertial sensors 31, 32a, 32b, 34a, 34b, 36a, 36b while the subject 1 is motionless and looking straight ahead.

Then, at block 706, the initial spatial orientation of the inertial sensors 31, 32a, 32b, 34a, 34b, 36a, 36b is computed from the AHRS data in view of the reference position obtained from the body sensor axes alignment process 300, 400, 500.

At block 708, gyroscopes data is acquired from the inertial sensors 31, 32a, 32b, 34a, 34b, 36a, 36b while the subject 1 is in motion, for example walking on the treadmill 18 of the biomechanical analysis and validation system 10 (see FIG. 1).

Finally, at block 710, the angular positions of lower limb segments of the subject 1 are computed by integrating the angular velocities over a 30 seconds period using the initial spatial orientation computed at block 706.

Referring to FIG. 18, there is shown a flow diagram of the third embodiment of the error reduction process 800 executed by the processor 22 (see FIG. 3). Steps of the process 800 are indicated by blocks 802 to 812.

The process 800 starts at block 802 where the subject 1 stands upright and motionless.

At block 804, accelerometer data is acquired from the inertial sensors 31, 32a, 32b, 349, 34b, 36a, 36b while the subject 1 is motionless and looking straight ahead.

Then, at block 806, the initial anteroposterior and transverse axis angular positions are determined from the accelerometer data.

At block 808, gyroscopes data is acquired from the inertial sensors 31, 32a, 32b, 34a, 34b, 36a, 36b while the subject 1 is in motion, for example walking on the treadmill 18 of the biomechanical analysis and validation system 10 (see FIG. 1).

At block 810, the longitudinal axis angular position is determined using the mean acceleration or rotation axis.

Finally, at block 812, the angular positions of lower limb segments of the subject 1 are computed by integrating the angular velocities over a 30 seconds period using the initial anteroposterior and transverse axis positions determined at block 806 and the longitudinal axis angular position determined at block 810.

It is to be understood that the error reduction processes 600, 700, 800 may be used independently of the biomechanical analysis and validation system 10 and incorporated into other applications.

Biomechanical Analysis

Figure 20:
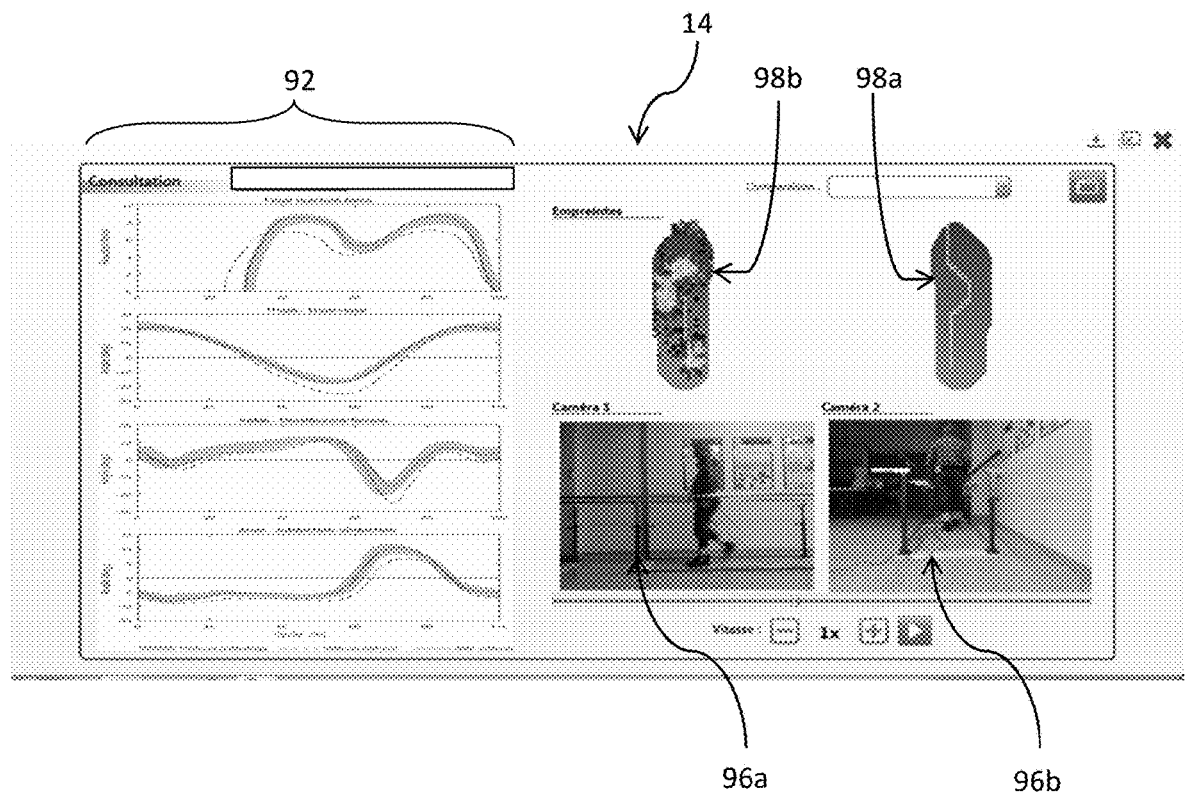
FIG. 20 is an example of a user interface of the biomechanical analysis and validation system of FIG. 1.

Referring to FIG. 20, the user interface/display 14 of the biomechanical analysis and validation system 10 includes synchronized display areas 92, 96a, 96b, 98a, 98b showing various biomechanical information 92 about the subject 1, real-time motion capture visualization of the subject's 1 locomotion in the anteroposterior 96a and transversal 96b axes from respective cameras 16a, 18b, as well as plantar pressure mapping for the right 98a and left 98b foot from respective plantar pressure sensors 38a, 38b, which allows the monitor of the evolution in time of the subject's 1 foot pressure pattern to identify biomechanical dysfunctions (i.e. pathologies) or drifts.

Figure 21:
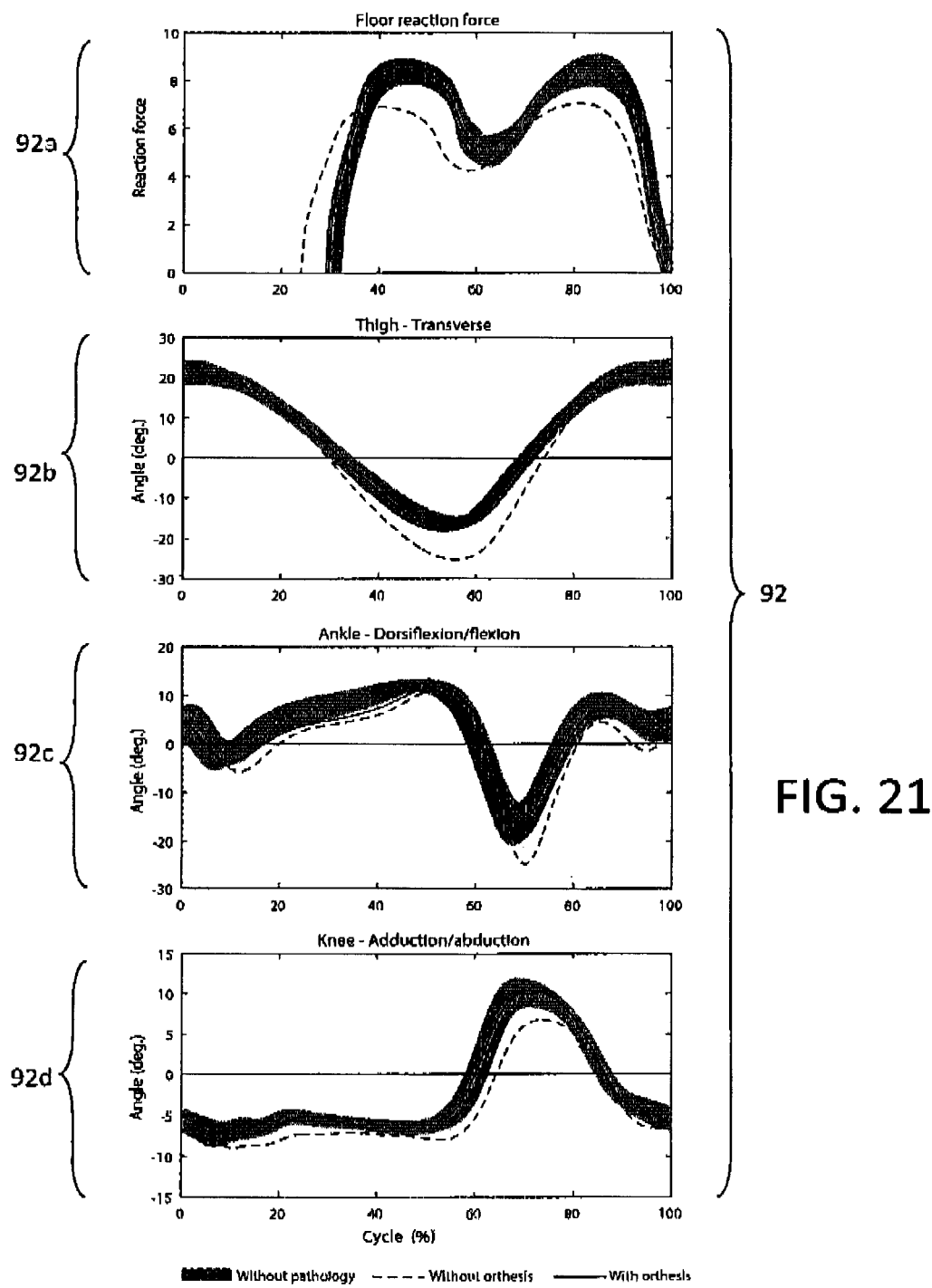
FIG. 21 is a detailed view of the user interface of FIG. 20.

Referring to FIG. 21, there is shown an example of displayed biomechanical information 92, which includes floor reaction force during walking 92a, thigh transverse angle 92b, ankle dorsiflexion/flexion 92c and knee adduction/abduction 92d, for both with or without the orthosis 11, each plotted along with a standard curve interval for a comparable subject, for example stored in the database 40, in order to help a user compare the subject's 1 biomechanical information 92, with and without the orthosis 11, with non-pathological curves.

It is to be understood that the number and nature of the displayed biomechanical information 92 may be fixed or user selectable. Table 1 illustrates the various biomechanical information 92 that can be displayed.

TABLE 1

Examples of biomechanical Information that can be displayed

| | | Angles | | |
|---|---|---|---|---|
| Segments | Pelvis | Transverse | Anteroposterior | Longitudinal |
| | Thigh | Transverse | Anteroposterior | Longitudinal |
| | Shank | Transverse | Anteroposterior | Longitudinal |
| | Foot | Transverse | Anteroposterior | Longitudinal |
| Joints | Hip | Flexion/ extension | Adduction/ abduction | Internal/ external |
| | Knee | Flexion/ extension | Adduction/ abduction | Internal/ external |
| | Ankle | Dorsiflexion/ plantar flexion | Supination/ pronation | Adduction/ abduction |

In an alternative embodiment, the database 40 may provide the biomechanical analysis and validation system 10 with decision support capabilities in order to support a user in establishing a diagnosis (i.e. detecting/identifying biomechanical dysfunctions) by cross-referencing various biomechanical information 92 of the subject 1 as well as comparing this information with biomechanical information from comparable subjects.

The result of the biomechanical information 92 of each subject 1 can be stored, for example in the database 40, for future reference and follow up on the subject's 1 progress. Past biomechanical information curves can be displayed along the present biomechanical information 92 in order to evaluate the progression of the subject 1, i.e. validate an orthotic solution provided to the subject or evaluate the effects of a corrective surgery.

The subject's 1 locomotion can be further decomposed into its various phases and states using, for example, the method disclosed in U.S. Pat. No. 7,147,667 entitled "Control System and Method for Controlling an Actuated Prosthesis" by Victhom Human Bionics Inc, which uses signals from the planter pressure sensors 38a, 38b (In this case numbering four, two under each foot) in order to breakdown the human locomotion.

Orthosis Fabrication Validation

Figure 22:
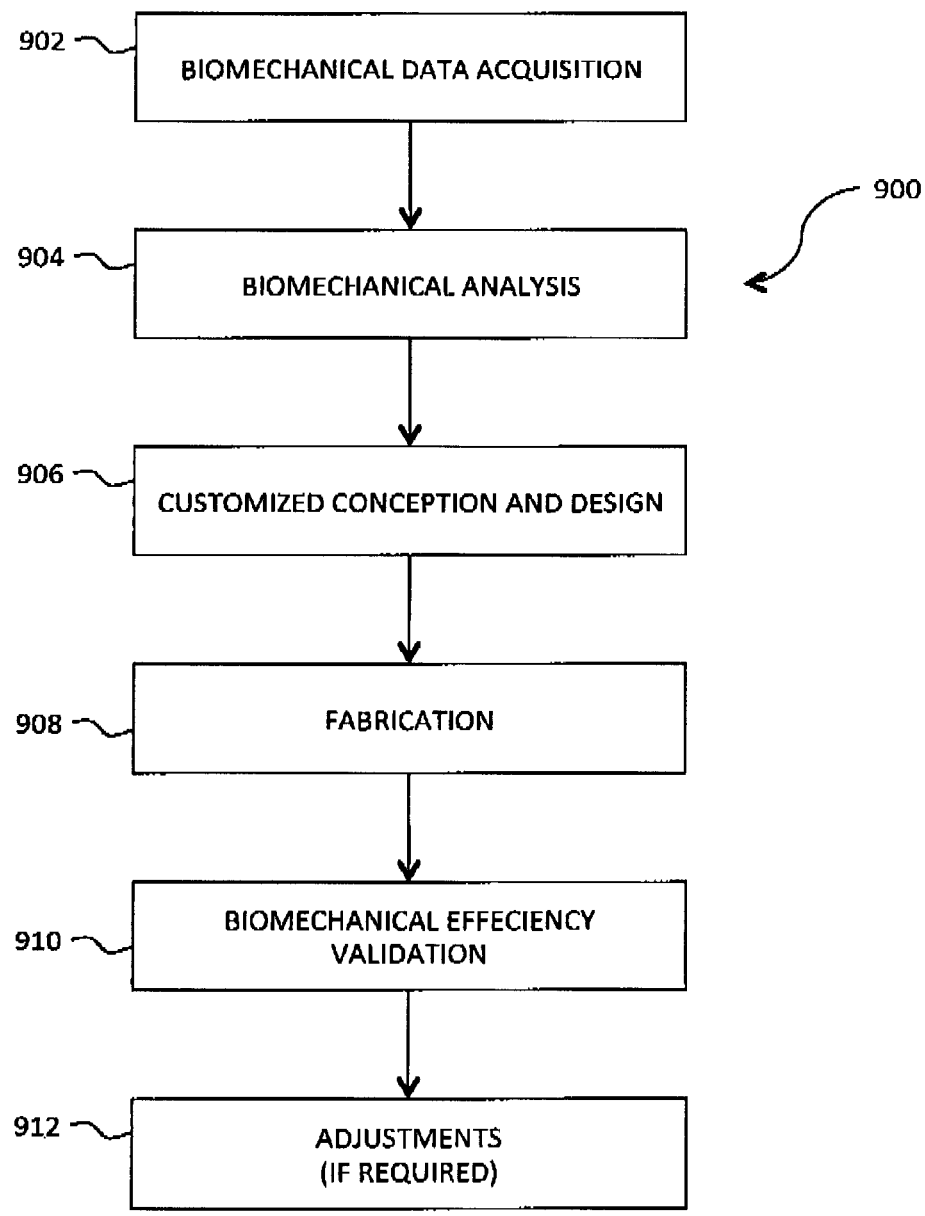
FIG. 22 is a flow diagram of the orthosis validation process in accordance with an illustrative embodiment of the present disclosure.

The biomechanical analysis and validation system 10 can be used in an orthosis fabrication process in order to validate the effectiveness of the produced orthosis. Referring to FIG. 22, there is shown a flow diagram of the biomechanical analysis and validation process 900. Steps of the process 900 are indicated by blocks 902 to 912.

The process 900 starts at block 902 where biomechanical data of a subject 1 fitted with the inertial sensors 31, 32a, 32b, 34a, 34b. 36a, 36b and planter pressure sensors 38a, 38b (see FIGS. 1 and 2) is obtained, from which, at block 904, the biomechanical information 82 of the subject 1 is displayed for analysis.

From this biomechanical information 92, at block 906, an orthosis 11 (i.e. knee brace, foot orthosis, etc., or combination thereof) is conceptualized and designed using the biomechanical information 92 of the subject 1 and biomechanical information from comparable subjects from the database 40 in order to correct an identified biomechanical dysfunction.

At block 908, an orthosis 11 is fabricated.

Then, at block 910, the biomechanical data 92 of the subject 1 is obtained anew while he is fitted with the orthosis 11 in order to validate the effectiveness of the orthosis 11 in correcting the identified biomechanical dysfunction.

Finally, at block 912, adjustments to the orthosis 11 are effectuated, if required.

It is to be understood that blocks 908 and 910 may be repeated a number of times until such a time the effectiveness of the orthosis is satisfactory.

It is to be further understood that, in an alternative embodiment, the biomechanical analysis and validation system 10 can be adapted so as to measure the angles of the upper body segments and joints. Furthermore, the biomechanical analysis and validation system 10 can be used to of body positioning analysis, for example in order to analyze the positioning of pilots in cockpit, ergonomic evaluation of workstations, etc.

Although the present disclosure has been described by way of particular non-limiting illustrative embodiments and examples thereof, it should be noted that it will be apparent to persons skilled in the art that modifications may be applied to the present particular embodiment without departing from the scope of the present disclosure as hereinafter claimed.

We claim:

1. A method for providing biomechanical information of a subject, comprising the steps of:
   positioning inertial sensors at the pelvis, the right and the left thighs, the right and the left shanks and the right and the left feet of the subject;
   aligning lower body segments of the subject in a global reference system ($X_g$, $Y_g$, $Z_g$), where $X_g$ is defined by the anteroposterior axis, $Y_g$ is defined by the gravity vector and $Z_g$ is perpendicular to $X_g$ and $Y_g$;
   determining a quaternion $q_s^g$ expressing an orientation of the lower body segments of the subject with respect to the global reference system;
   determining the orientation of the $Y_g^b$ axis of the inertial sensors with respect to the global reference system;
   determining the orientation of the $X_g^b$ axis of the inertial sensors with respect to the global reference system;
   determining the orientation of the $Z_g^b$ axis by calculating the vector product $Z_g^b = X_g^b \times Y_g^b$;
   determining a quaternion $q_g^b$ expressing a change of reference from the global reference system to a reference of the inertial sensors from $Y_g^b$, $X_g^b$ and $Z_g^b$;
   determining a quaternion $q_b^s$ expressing a change of reference of the inertial sensors with regard to the lower body segments of the subject by calculating $q_b^s = (q_b^g \cdot q_s^g)^*$;
   initializing gyroscopes of the inertial sensors using the reference of the inertial sensors with regard to the lower body segments of the subject;
   calculating angles of the lower body segments of the subject during a transition phase from a sitting posture to a standing posture of the subject using the data from the inertial sensors, providing an orientation of the lower body segments of the subject in the standing posture $q_{s_0}^g$ to be used as an initial value when recording locomotion cycle sessions of the subject;
   providing the angles of the lower body segments of the subject.

2. The method of claim 1, wherein the step of determining the orientation of the $Y_g^b$ axis of the inertial sensors with respect to the global reference system is performed by calculating a mean acceleration vector from accelerometer data provided by the inertial sensors while the subject is motionless.

3. The method of claim 1, wherein the step of determining the orientation of the $X_g^b$ axis of the inertial sensors with respect to the global reference system is performed by moving the subject in an anteroposterior axis and finding an axis that best fits a point cloud of the accelerometer data from the inertial sensors.

4. The method of claim 1, wherein the calculating of the mean acceleration vector from accelerometer data is performed by acquiring the accelerometer data during a plurality of periods of one second and calculating the mean acceleration vector over one of the plurality of periods of one second having the smallest variance.

5. The method of claim 1, wherein the angles of the lower body segments of the subject in the standing posture is performed by acquiring the data from the inertial sensors during a plurality of periods of one second and selecting one of the plurality of periods of one second having the smallest variance.

6. The method of claim 1, further comprising the step of providing biomechanical information of the subject based on the angles of the lower body segments of the subject while the subject is performing a locomotion cycle session.

7. The method of claim 6, wherein the biomechanical information is selected from a group consisting of thighs transverse angle information, ankles dorsiflexion/flexion information and knee adduction/abduction information.

8. The method of claim 6, wherein the biomechanical information is provided along with a standard curve interval for a comparable subject.

9. The method of claim 6, further comprising the steps of positioning plantar pressure sensors under the right and the left foot of the subject and wherein the provided biomechanical information includes plantar pressure mapping for the right and the left foot of the subject from pressure information provided by the respective right foot and left foot plantar pressure sensors.

10. The method of claim 6, wherein further comprising the steps of:
    providing biomechanical information of the subject based on the angles of the lower body segments of the subject while the subject is performing a locomotion cycle session while wearing an orthosis;
    validating an effect of the orthosis by comparing the biomechanical information of the subject provided while the subject is performing a locomotion cycle session with the biomechanical information of the subject provided while the subject is performing a locomotion cycle session while wearing the orthosis.

11. The method of claim 1, wherein the step of aligning the lower body segments of the subject in the global reference system includes the substeps of:
    providing a body alignment system consisting of an adjustable height stool, a movable base, a right and a left foot positioning blocks and a right and a left knee spacers having a height adjustment mechanism;
    having the subject sit on the adjustable height stool;
    adjusting the eight of the adjustable height stool so that the subject's thighs are horizontal and the subject's shanks are vertical, with respect to the movable base, with the subject's feet aligned using the foot positioning blocks and the subject's knees are resting against the knee spacers;
    positioning anatomical reference markers on the lower body segments of the subject at:
    the greater trochanter (GT);
    the lateral epicondyle (LE);
    the head of the fibula (HF);
    the lateral malleolus (LM);
    the anterior superior iliac spine (ASIS);
    the center of the patella (CP);

positioning as a reference marker at the center of the foot positioning blocks (CFPB);

projecting a horizontal and a vertical laser leveling beams on a side of the subject so as to pass by the LE and HF anatomical reference markers, respectively;

adjusting the position of the thighs of the subject by adjusting a height of the adjustable height stool such that the GT anatomical reference marker is level with the horizontal laser leveling beam;

adjusting the position of the shanks of the subject by adjusting a position of the foot positioning blocks such that the LM anatomical reference marker is level with the vertical laser leveling beam;

projecting a front of the subject vertical laser leveling beam so as to pass by the ASIS anatomical reference marker, the VLB vertical laser leveling beam being positioned such as to project a plan that is coplanar with the anteroposterior axis;

adjusting the position of the knees of the subject by adjusting the knee spacers such that the CP anatomical reference marker is level with the vertical laser leveling beam;

adjusting the position of the feet of the subject by adjusting the foot positioning blocks such that the CFPB reference marker is level with the vertical laser leveling beam VLB;

defining the quaternion $q_s^g$ of the orientation of the body segments of the subject with respect to the global reference system.

12. The method of claim 6, further comprising the step of reducing error by:

acquiring accelerometer data from the inertial sensors while the subject is motionless and looking straight ahead;

determining an initial spatial orientation of the subject using a gravity vector obtained from the accelerometer data;

acquiring gyroscope data from the inertial sensors is acquired from the inertial sensors while the subject is in motion;

computing angular positions of lower limb segments of the subject by integrating the angular velocities from inertial sensors over a 30 seconds period using the initial spatial orientation.

13. The method of claim 6, further comprising the step of reducing error by:

acquiring attitude and heading reference systems (AHRS) data from the inertial sensors while the subject is motionless and looking straight ahead;

computing the initial spatial orientation of the inertial sensors from the AHRS data in view of the reference of the inertial sensors with regard to the lower body segments of the subject;

acquiring gyroscope data from the inertial sensors while the subject is in motion;

computing the angular positions of lower limb segments of the subject by integrating the angular velocities from inertial sensors over a 30 seconds period using the initial spatial orientation.

14. The method of claim 6, further comprising the step of reducing error by:

acquiring accelerometer data from the inertial sensors while the subject is motionless and looking straight ahead;

determining an initial anteroposterior and transverse axis angular positions using the accelerometer data;

acquiring gyroscope data is acquired from the inertial sensors while the subject is in motion;

determining the longitudinal axis angular position using the mean acceleration or rotation axis;

computing the angular positions of the lower limb segments of the subject by integrating the angular velocities from inertial sensors over a 30 seconds period using the initial anteroposterior and transverse axis positions determined and the longitudinal axis angular position.

15. A method of aligning lower body segments of a subject in a global reference system, comprising the steps of:

providing a body alignment system consisting of an adjustable height stool, a movable base, a right foot positioning block and a left foot positioning block and a right knee spacer and a left knee spacer having a height adjustment mechanism;

having the subject sit on the adjustable height stool;

adjusting a height of the adjustable height stool so that the subject's thighs are horizontal and the subject's shanks are vertical, with respect to the movable base, with the subject's feet aligned using the foot positioning blocks and the subject's knees are resting against the knee spacers;

positioning anatomical reference markers on the lower body segments of the subject at:
the greater trochanter (GT);
the lateral epicondyle (LE);
the head of the fibula (HF);
the lateral malleolus (LM);
the anterior superior iliac spine (ASIS);
the center of the patella (CP);

positioning as a reference marker at the center of the foot positioning blocks (CFPB);

projecting a horizontal laser leveling beam and a vertical laser leveling beam on a side of the subject so as to pass by the LE and HF anatomical reference markers, respectively;

adjusting a position of the thighs of the subject by adjusting a height of the adjustable height stool such that the GT anatomical reference marker is level with the horizontal laser leveling beam;

adjusting a position of the shanks of the subject by adjusting a position of the foot positioning blocks such that the LM anatomical reference marker is level with the vertical laser leveling beam;

projecting a front of the subject vertical laser leveling beam so as to pass by the ASIS anatomical reference marker, the VLB vertical laser leveling beam being positioned such as to project a plan that is coplanar with the anteroposterior axis;

adjusting a position of the knees of the subject by adjusting the knee spacers such that the CP anatomical reference marker is level with the vertical laser leveling beam;

adjusting a position of the feet of the subject by adjusting the foot positioning blocks such that the CFPB reference marker is level with the vertical laser leveling beam VLB;

defining a quaternion $q_s^g$ of an orientation of the body segments of the subject with respect to a global reference system.

* * * * *